(12) United States Patent
Illmann et al.

(10) Patent No.: US 8,379,949 B2
(45) Date of Patent: Feb. 19, 2013

(54) METHOD AND APPARATUS FOR PREPROCESSING AND STORING IMAGE ATTRIBUTES FOR THE ACCELERATED DISPLAY OF MEDICAL IMAGES IN MEDICAL APPLICATIONS

(75) Inventors: Joerg Illmann, Burgthann (DE); Michael Pisot, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 199 days.

(21) Appl. No.: 13/013,872

(22) Filed: Jan. 26, 2011

(65) Prior Publication Data
US 2011/0216950 A1    Sep. 8, 2011

(30) Foreign Application Priority Data
Mar. 4, 2010   (DE) .......................... 10 2010 010 195

(51) Int. Cl.
*G06K 9/00*   (2006.01)
*B41M 5/00*   (2006.01)
(52) U.S. Cl. ........................... 382/128; 382/305; 378/29
(58) Field of Classification Search .................. 382/100, 382/103, 128, 129, 130, 131, 132, 133, 134, 382/155, 162, 168, 173, 181, 189, 209, 224, 382/232, 254, 274, 276, 305, 312; 1/1; 378/21, 378/62, 29
See application file for complete search history.

(56) References Cited

U.S. PATENT DOCUMENTS

| | | | | |
|---|---|---|---|---|
| 5,740,267 | A * | 4/1998 | Echerer et al. | 382/132 |
| 6,574,629 | B1 * | 6/2003 | Cooke, Jr. et al. | 1/1 |
| 7,269,303 | B2 * | 9/2007 | Miller et al. | 382/305 |
| 7,596,252 | B2 * | 9/2009 | Hasselberg | 382/128 |
| 7,945,083 | B2 * | 5/2011 | Zhang et al. | 382/132 |
| 8,189,888 | B2 * | 5/2012 | Takahashi | 382/128 |

* cited by examiner

*Primary Examiner* — Seyed Azarian
(74) *Attorney, Agent, or Firm* — Harness, Dickey & Pierce, P.L.C.

(57) ABSTRACT

A method and apparatus are disclosed for preprocessing and storing image attributes for the accelerated display of medical images in medical applications. In at least one embodiment, the method includes: assigning image attributes to a medical image, which are characteristic of a medical application which generates a specific visual display of the medical image; adjusting the medical image in accordance with the image attributes; storing the adjusted medical image together with the image attributes; calling up a further or the same medical application, which requires a visual display of the medical image; checking whether the required image attributes for the visual display correspond to the stored image attributes; calling up the stored, modified medical image in the case of a similar or identical correspondence of the image attributes; and visually displaying the recalled medical image.

3 Claims, 1 Drawing Sheet

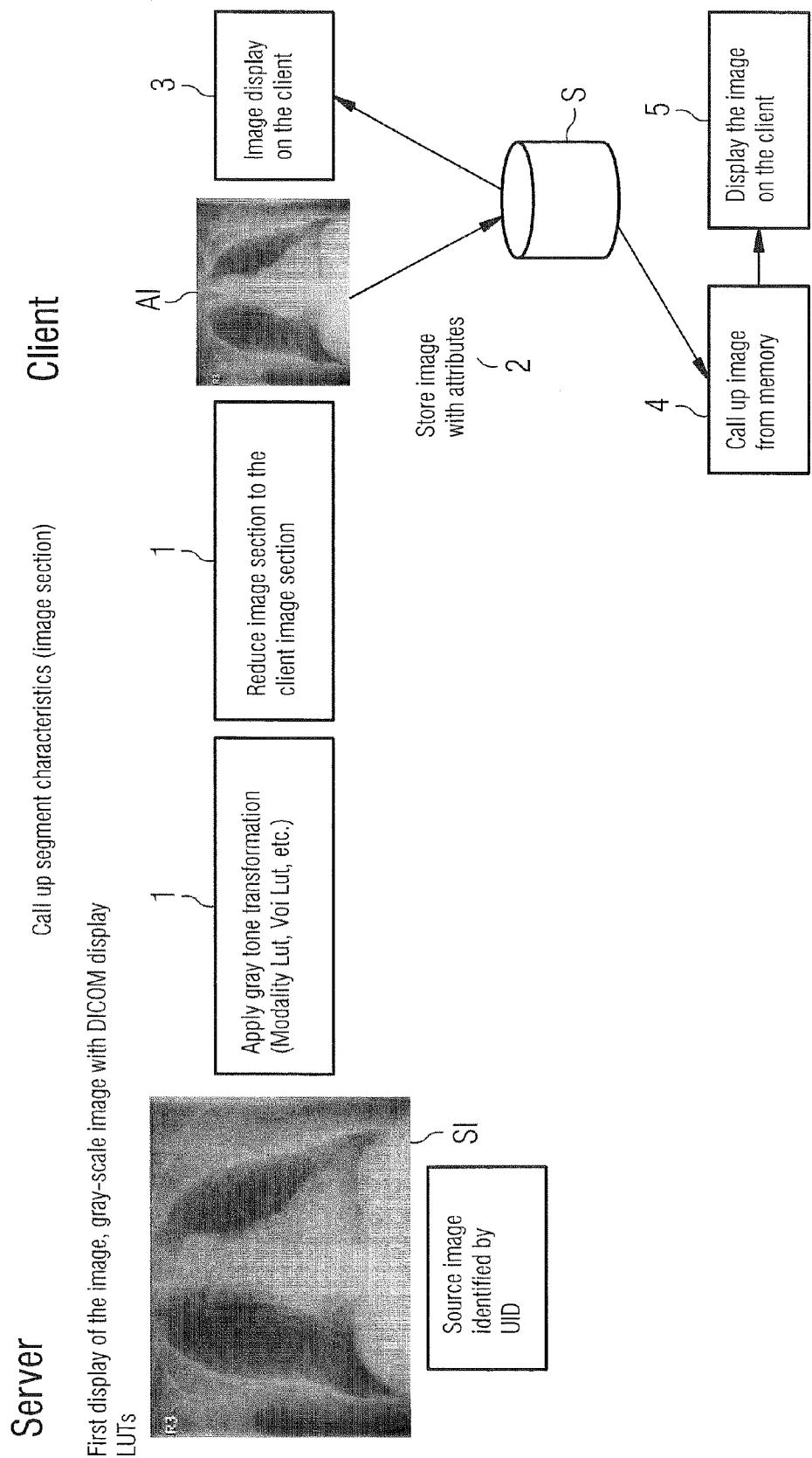

METHOD AND APPARATUS FOR PREPROCESSING AND STORING IMAGE ATTRIBUTES FOR THE ACCELERATED DISPLAY OF MEDICAL IMAGES IN MEDICAL APPLICATIONS

PRIORITY STATEMENT

The present application hereby claims priority under 35 U.S.C. §119 on German patent application number DE 10 2010 010 195.8 filed Mar. 4, 2010, the entire contents of which are hereby incorporated herein by reference.

FIELD

At least one embodiment of the invention generally relates to a method for preprocessing and storing image attributes for accelerated image display in medical applications as well as an associated apparatus.

BACKGROUND

High demands are placed on the visual display and processing in medical applications in order to be able to represent large medical images and/or image data. Although the final display is comparatively small, large source data is processed and immediate image results are expected. In the medical field, a so-called client server architecture prevails for the processing, display and storage of medical images. This means that large image data is frequently transferred to and fro between the users, i.e. a client computer, and a server, i.e. a central unit. If adjustments are to be made to the image characteristics on the client side, image data is frequently called up from the server in the direction of the client and vice versa, which is costly in terms of time and resources.

SUMMARY

In at least one embodiment of the invention, rapid image display on the client, which can be implemented as quickly and with as few resources as possible, is achieved.

At least one embodiment of the invention is directed to a method and/or an apparatus according to the independent claims. Advantageous embodiments of the method and the apparatus form the subject matter of the dependent claims and can be inferred from the subsequent description and exemplary embodiments.

In at least one embodiment, the invention allows for several attributes to be assigned to each image, which is to be processed and represented. These attributes include mandatory attributes, i.e. the source image frame is identified, and optional attributes, i.e. the processing algorithm applied to the image is identified.

Mandatory attributes may include, for instance:

Each medical image frame which is processed and displayed is provided with a so-called unique identifier ID and a frame number. According to the DICOM standard for medical images, the attribute SopinstanceUid is usually used as a global unique identifier. The DICOM frame number identifies the frame within the image. This unique identifier is considered to be a mandatory attribute of a medical image.

Optional attributes may include, for instance:

These attributes identify the so-called viewport (i.e. the image section) and characteristics for segment display. These may include, for instance:

the size of the segment, which is used to display the image,
the scaling factor, which identifies the resolution of the image to displayed,
the so-called viewport, which identifies the part of the image which is to be displayed.

Further attributes of at least one embodiment may depend on the processing steps, which are applied to the image. These may contain for instance:

displaying the gray scale values applied, which are reflected in DICOM in the attributes Modality LuT (LuT: Look up Table) and Voi LuT Sequence.
geometric information operators, which are applied to the image, e.g. angle of rotation and reversal of the image,
display attributes like the shutter used and the display variables,
color palette applied, which corresponds to the DICOM Color LuT Identifier attribute.

At least one embodiment of the invention may then be primarily applied when large medical images are displayed on a client computer or are transmitted hereto. Furthermore, at least one embodiment of the invention may be applied when a rapid display of the images is required within a video sequence.

At least one embodiment of the invention may include at least one of the following advantages:

The display performance may be significantly improved as a result of the inventive approach described above. The speed performance may be significantly increased for image sequences by way of video sequences of ultrasound images. A high frequency of several image frames may be achieved. Lower levels of data transfer and loading of the computer network may be achieved. The load on the user interface may be reduced by lower levels of pixel buffering. As a result, an improved resource consumption and a faster display performance may be achieved.

BRIEF DESCRIPTION OF THE DRAWINGS

Further advantages, details and developments of the invention emerge from the subsequent description of example embodiments in conjunction with the drawing.

In the drawing, the FIGURE shows a schematic flow diagram of the inventive procedure.

DETAILED DESCRIPTION OF THE EXAMPLE EMBODIMENTS

Various example embodiments will now be described more fully with reference to the accompanying drawing in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawing and will herein be described in detail. It should be understood, however, that there is no intent to limit example embodiments of the present invention to the particular forms disclosed. On the contrary, example embodiments are to cover all modifications, equivalents, and alternatives falling within the scope of the invention.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The FIGURE shows a server and a client. The server receives segment characteristics from the client, i.e. a selection of an image section (viewport). The image is firstly displayed as a gray-scale image with the DICOM display attributes. The source image SI is uniquely identified by the identifier UID. In step 1 of the FIGURE a gray tone transformation is used. In step 2 the original image is restricted to the image section which has been selected on the client side. The original image is then stored with the modified image attributes as a modified image AI in a memory S or a database. Step 3 shows the image on the client side. In the event that the image is to be displayed subsequently in some instances in an image sequence, a check is carried out to determine whether the original image SI with the necessary attributes has already been stored. If so, the image is called up from the memory (step 4 and step 5) and displayed on the client side.

Server configurations and interaction status, as well as transformations are used on the server as a function of the image type. Attributes, which have stored these transformations with the image, include for instance geometric transformations (restriction to the image section, rotation etc,) and gray tone display (DICOM attributes Modality LuT, Voi LuT and Presentation LuT). In this way an image is preprocessed in accordance with the desired display characteristics and is stored in a memory together with the describing image attributes. When an image sequence is to be displayed, the image section and the display parameters are called up from the client. The server uses the parameters to process the image, as it is expected to be displayed on the client. The preprocessed image is stored with the attributes and its visual appearance filed in a cache memory on the server side.

Alternative approaches may include:

Buffering the preceding images without transformation of the attributes. This requires a time-consuming pixel to pixel comparison in order to be able to identify image parities, and a buffering of previous images, without making use of the image section attributes defined on the client side. This requires larger images to be processed on the client side and transmitted in the network.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

SI Source image
AI Modified image
S Memory
1, 2, 3, 4, 5 Method steps

What is claimed is:

1. A method for preprocessing and storing image attributes for the accelerated display of medical images in medical applications, comprising:
   a) assigning image attributes to a medical image, the image attributes being characteristic of a medical application which generates a specific visual display of the medical image;
   b) adjusting the medical image in accordance with the assigned image attributes;
   c) storing the adjusted medical image together with the image attributes;
   d) calling up a further medical application or the medical application, which requires a visual display of the medical image;
   e) checking whether the required image attributes for the visual display in step d) correspond to the stored image attributes in step c);
   f) calling up the stored, modified medical image upon the checking indicating a similar or identical correspondence of the image attributes; and
   g) visually displaying the called up modified medical image,
      wherein the image attributes include mandatory attributes and optional attributes, the mandatory attributes including a source image frame identifier and the optional attributes including particular identifiers of one or several processing algorithms applied to the medical image for visual display purposes.

2. A non-transitory computer readable medium including program segments for, when executed on a computer device, causing the computer device to implement the method of claim 1.

3. A client apparatus for preprocessing and storing image attributes for the accelerated display of medical images in medical applications, the client apparatus being capable of communicating with at least one server apparatus, comprising:
   means for receiving image attributes assigned on the server side to a medical image, the image attributes being characteristic of a medical application which generates a specific visual display of the medical image;
   means for adjusting the medical image in accordance with the image attributes;
   means for storing the adjusted medical image together with the image attributes in a memory or a database;
   means for calling up a further medical application or the medical application, which requires a visual display of the medical image;
   means for checking whether the required image attributes for the visual display correspond to the stored image attributes;
   means for calling up the stored, modified medical image upon the checking indicating a similar or identical correspondence of the image attributes; and
   means for the visually displaying the called up medical image,
   wherein the image attributes include mandatory attributes and optional attributes, the mandatory attributes including a source image frame identifier and the optional attributes including particular identifiers of one or several processing algorithms applied to the medical image for visual display purposes.

* * * * *

UNITED STATES PATENT AND TRADEMARK OFFICE
CERTIFICATE OF CORRECTION

| | |
|---|---|
| PATENT NO. | : 8,379,949 B2 |
| APPLICATION NO. | : 13/013872 |
| DATED | : February 19, 2013 |
| INVENTOR(S) | : Jörg Illmann et al. |

It is certified that error appears in the above-identified patent and that said Letters Patent is hereby corrected as shown below:

Title Page, Item (75) Inventors should read as follows: Jörg Illmann, Burgthann (DE); Michael Pisot, Erlangen (DE)

Signed and Sealed this
Eleventh Day of June, 2013

Teresa Stanek Rea
*Acting Director of the United States Patent and Trademark Office*